United States Patent
Yang et al.

(10) Patent No.: US 6,884,401 B2
(45) Date of Patent: Apr. 26, 2005

(54) METHOD FOR REMOVING VOLATILE COMPONENTS FROM A HIGH VISCOSITY LIQUID BY USING ROTATION PACK BED

(75) Inventors: Sheng Yang, Hsinchu (TW); Chia-Chang Lin, Hsinchu (TW); I-Min Tseng, Hsinchu (TW); Wen-Tzong Liu, Hsinchu (TW); Hua-Tang Yu, Hsinchu (TW)

(73) Assignee: Industiral Technology Research Institute, Hsinchu (TW)

( * ) Notice: Subject to any disclaimer, the term of this patent is extended or adjusted under 35 U.S.C. 154(b) by 343 days.

(21) Appl. No.: 10/196,245

(22) Filed: Jul. 17, 2002

(65) Prior Publication Data

US 2004/0015003 A1 Jan. 22, 2004

(51) Int. Cl.⁷ .......................... B01D 33/06; B01B 7/01; C01F 9/02
(52) U.S. Cl. .................. 423/240 S; 423/240 R; 95/155; 95/261; 95/263; 96/202; 96/216; 96/214; 96/196; 528/44; 558/90; 558/95
(58) Field of Search ................ 423/240 R, 240 S; 95/155, 261, 263; 96/202, 216, 214, 196; 528/502 D, 44; 585/600, 90, 95

(56) References Cited

U.S. PATENT DOCUMENTS

| | | | |
|---|---|---|---|
| 3,823,207 A | 7/1974 | Herzog et al. | 260/976 |
| 4,283,255 A | 8/1981 | Ramshaw et al. | 203/49 |
| 4,382,045 A | 5/1983 | Wem | 261/89 |
| 4,382,900 A | 5/1983 | Wem | 261/89 |
| 4,400,275 A | 8/1983 | Ramshaw et al. | 210/321.1 |
| 4,715,869 A | * 12/1987 | Ramshaw | 95/263 |
| 5,531,904 A | * 7/1996 | Grisham et al. | 210/703 |
| 6,048,513 A | 4/2000 | Quarderer et al. | 423/473 |
| 6,730,214 B2 | * 5/2004 | Mazzei | 210/188 |

FOREIGN PATENT DOCUMENTS

CN 1116146 2/1996

* cited by examiner

Primary Examiner—Ngoc-Yen Nguyen
(74) Attorney, Agent, or Firm—Bacon & Thomas PLLC

(57) ABSTRACT

A high viscosity liquid is fed into a rotation pack bed at a position with a distance far enough from a rotation axis, creating a centrifugal force exerted on the high viscosity liquid overwhelming a drag thereof, so that it can flow radially through the rotation pack bed. A high pressure gas is introduced into the rotation pack bed peripherally and/or a suction force source is connected to a position near the rotation axis, so that a volatile component contained in the high viscosity fluid is entrained in the gas counter currently flowing through the rotation pack bed and withdrawn from the position near the rotation axis, or the volatile component exits from the position near the rotation axis in gas phase, and thus the volatile component is removed from the high viscosity liquid. A second fluid can also be fed into the rotation pack bed to react with the high viscosity liquid, so that a reaction product is formed, and a volatile side product is removed at the same time.

8 Claims, 1 Drawing Sheet

METHOD FOR REMOVING VOLATILE COMPONENTS FROM A HIGH VISCOSITY LIQUID BY USING ROTATION PACK BED

FIELD OF THE INVENTION

The present invention relates to a mass transport device, particularly a rotation pack bed, and a method for removing volatile components from a high viscosity liquid.

BACKGROUND OF THE INVENTION

Triarylphosphite $P(OAr)_3$ is an additive commonly used in the plastic processing as an antioxidant, wherein Ar represents an aryl group. A conventional method for preparing this antioxidant comprises a chemical reaction step and a step of removing by-products. The two steps are separately described herein below:

Chemical Reaction Step:

To a batch agitation tank an ArOH liquid is added, and $PCl_3$ is slowly added into the tank while stirring. The chemical reactions carried out in the tank are shown in the following:

$$ArOH + PCl_3 \rightleftharpoons ArOPCl_2 + HCl \quad (1)$$

$$ArOH + ArOPCl_2 \rightleftharpoons (ArO)_2PCl + HCl \quad (2)$$

$$ArOH + (ArO)_2PCl \rightleftharpoons (ArO)_3P + HCl \quad (3)$$

The by-product HCl in the formulas (1), (2) and (3) is a volatile gas. The HCl gas makes a large amount of foams in the viscous reaction liquid, creating an overflow from the tank, so that the batch agitation tank is not allowed to accept feeds continuously and rapidly. As a result, the retention time of a batch of 4 tons requires more than 10-hours processing.

Step of Removing By-Product:

The by-product HCl generated during the chemical reaction step must be removed from the reaction system, thereby breaking the equilibrium of the chemical reaction and increasing the yield of the anti-oxidant $P(OAr)_3$. A conventional method of removing HCl comprises blowing an inert gas at normal pressure into the product mixture to an acid value of 3 mgKOH/g, then forming a vacuum and blowing an inert gas to the mixture again to a market acceptable acid value of 0.1 mgKOH/g. It takes more than 12 hours for removing HCl from the product mixture to the acid value of 0.1 mg KOH/g.

Herzog and Hoppe (U.S. Pat. No. 3,823,207) in 1974 has disclosed a method for preparing a triarylphosphite anti-oxidant, wherein a conventional batch process using an agitation tank is changed into a continuous process of an overflow-type reaction tank formed by a shallow dish added with a partition plate. The ratio of area to volume of the reaction region formed by the overflow partition plate is larger than that of a conventional agitation tank. A larger area to volume ratio can be formed when a reaction fluid passes through an overflow partition plate. This is beneficial to the contact of reactants and the removal of HCl gas. Furthermore, the reaction liquid is added with a high-boiling solvent, which is inert to $PCl_3$, in order to reduce the viscosity of the reaction liquid. The abovementioned improvement measures are used to increase the feeding rate of the raw materials. Even though the reaction retention time is shorter than that of the conventional batch process, the added solvent needs to be separated by a distillation process, thereby greatly increasing the energy consumption.

SUMMARY OF THE INVENTION

A primary objective of the present invention is to provide a method for removing volatile components from a high viscosity liquid by using a rotation pack bed.

Another objective of the present invention is to provide a method for preparing a product by using a rotation pack bed to conduct a reaction of a high viscous liquid and another fluid, while removing a volatile by-product at the same time.

In the present invention, a high viscosity liquid is fed into a rotation pack bed at a position with a distance far enough from a rotation axis, creating a centrifugal force exerted on the high viscosity liquid, which overwhelms a drag thereof, so that it can flow radially through the rotation pack bed.

Figure 1:
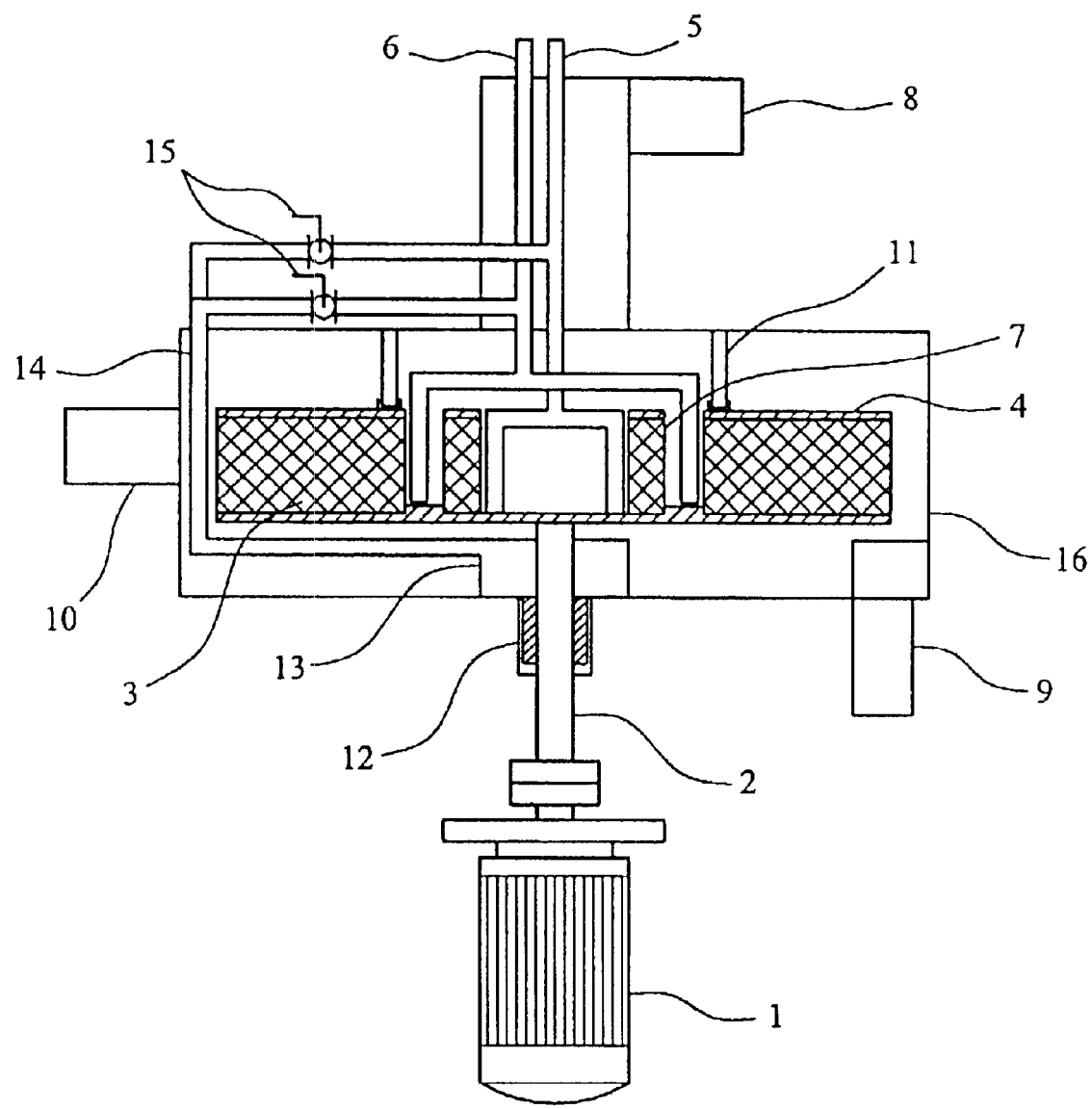
FIG. 1 is a schematic cross-sectional view of a multi-liquid-type rotation pack bed reaction system according to the present invention.

LEGENDS 1. driving motor
2. transmission shaft
3. pack bed
4. rotation drum
5. first liquid inlet
6. second liquid inlet
7. distribution dish
8. gas outlet
9. liquid outlet
10. gas inlet
11. sealing device
12. mechanical shaft seal
13. internal circulation pump
14. internal circulation pipeline
15. recycling ratio control valve

DETAILED DESCRIPTION OF THE INVENTION

An apparatus for performing mass transfer by counter currently contacting two fluids with different specific gravities was known by the persons skilled in the art, e.g. U.S. Pat. Nos. 4,283,255; 4,382,045; 4,382,900; and 4,400,275. China Patent Publication No. CN1116146A (1996) discloses a method for preparing ultra-fine particles by using said mass-transfer apparatus, wherein liquid streams are fed to an axis of a rotation pack bed through a distributor from the inner pipe and annular space of two concentric tubes, and contact and react with each other in the rotation pack bed by the centrifugal effect. U.S. Pat. No. 6,048,513 (2000) provides a process for preparing hypohalous acid by using a rotation pack bed, which comprises counter currently contacting a liquid reactant with a chlorine gas through a rotation pack bed rotating at a high speed; and separating the gas from the liquid. The process comprises adsorption, reaction and desorption. The rotation pack bed can increase the yield of the process to 90% compared to a yield of 80% of the conventional process, while using a gas flow 50% lower than that used by the conventional process. The viscosities of the liquid feeds in the abovementioned China Patent Publication No. CN1116146A and U.S. Pat. No. 6,048,513 are all very small (about 1 cp at 25° C.). Therefore, the liquid feeds still receive a sufficient rotation centrifugal field when fed at a location near the axis of the rotation pack bed, and flows radially through said pack bed.

In the abovementioned method for preparing the $P(OAr)_3$ antioxidant described in the Background of the Invention, the inventors of this application deem that overcoming the mass transfer limit of HCl in the viscous reaction fluid is a key factor in accelerating the production process, increasing the yield of the $P(OAr)_3$ antioxidant, and reducing the acid value of the $P(OAr)_3$ antioxidant. Therefore, the present inventors think of using a rotation pack bed to promote the reactants mixing and mass transfer rate of HCl in the viscous reaction liquid. However, if the highly viscous ArOH liquid is fed to the axis position of the rotation pack bed as in the conventional process, said highly viscous ArOH liquid will stay there due to its high viscosity and can not radially flow through the rotation pack bed. In order to solve this problem, the present inventors develop a novel rotation pack bed, wherein an inlet for said high viscosity liquid is installed at a location far enough from the axis in order to generate a sufficient centrifugal force to promote said high viscosity liquid flowing through said rotation pack bed.

The present inventors also provide a method for removing volatile components from a high viscosity liquid, e.g. removing an unreacted polyisocyanate monomer from a highly viscous polyurethane, and removing HCl from a high viscosity tris nonylphenol phosphite anti-oxidant.

A method for removing volatile components from a high viscosity liquid by using a rotation pack bed embodied according to the present invention comprising the following steps:

a) introducing a high viscosity liquid into a rotation pack bed rotating around an axis, said rotation pack bed being located in a housing and comprising a central channel region around said axis and an annular pack region surrounding said central channel region, said annular pack region being packed with a packing, and said annular pack region and said central channel region being in fluid communication only through a boundary thereof, and said annular pack region and said housing being in fluid communication only through an outer circumference of said annular pack region, wherein said high viscosity liquid is introduced to a location in said annular pack region so that said high viscosity liquid receives a sufficient centrifugal force at said location and can radially flow through said packing from said location in a direction away from said axis;

b) introducing a high pressure gas at a location near the outer circumference of said annular pack region, and/or connecting said central channel region to a suction source so that, when said highly viscous fluid radially flows through said packing, a volatile component in said high viscosity liquid together with said high pressure gas or said volatile component per se flow out of said rotation pack bed and said housing in a gas phase from said central channel region; and c) collecting a purified liquid, which flows out from the outer circumference of said annular pack region, from a bottom of said housing.

Said high viscosity liquid in step a) of the method of the present invention preferably has a viscosity less than 3000 cps at room temperature.

Preferably, said high viscosity liquid in step a) comprises tris nonylphenol phosphite, and hydrogen chloride contained in said tris nonylphenol phosphite, wherein said volatile component is said hydrogen chloride, and said purified liquid is a tris nonylphenol phosphite having a reduced amount of hydrogen chloride.

Preferably, said high viscosity liquid in step a) comprises polyurethane and an unreacted polyisocyanate monomer contained in said polyurethane, wherein said volatile component is said polyisocyanate monomer, and said purified liquid is a polyurethane having a reduced amount of polyisocyanate monomer.

Preferably, in step b), a high pressure nitrogen gas is introduced into said housing as said high pressure gas.

Preferably, the method of the present invention further comprises recycling a portion of the purified liquid in step c) to step a) and into said annular pack region.

Preferably, in step b), a high pressure gas is introduced into said housing, which contacts and reacts with the high viscosity liquid when said high viscosity liquid is radially flowing through said packing material, wherein a product of the chemical reaction together with unreacted high pressure gas flows out said rotation pack bed and said housing in a gas phase from said central channel region, and another product of the chemical reaction is collected at the bottom of said housing together with unreacted high viscosity liquid.

Preferably, step a) further comprises introducing a liquid reactant from said central channel region to said rotation pack bed, said liquid reactant flowing through said packing in a radial direction away from said axis by a centrifugal force, and said liquid reactant and said high viscosity liquid generating a chemical reaction, wherein a product of the chemical reaction flows out of said rotation pack bed and said housing in a gas phase, and another product of the chemical reaction, unreacted high viscosity liquid and unreacted liquid reactant are collected at the bottom of said housing. More preferably, in step b), an inert gas is introduced into said housing as the high pressure gas. Said product of the chemical reaction together with said high pressure inert gas flows out of said rotation pack bed and said housing in a gas phase through said central channel region; and said another product of the chemical reaction and the unreacted high viscosity liquid and the unreacted liquid reactant are collected at the bottom of said housing. For example, said high viscosity liquid comprises nonylphenol, said liquid reactant comprises $PCl_3$, said high pressure inert gas is nitrogen, one product of the chemical reaction is HCl which flows out of said rotation pack bed from said central channel region in a gas phase together with the nitrogen, and another product of the chemical reaction is tris nonylphenol phosphite which, together with unreacted nonylphenol and $PCl_3$, is collected at the bottom of said housing.

As shown in FIG. 1, a multi-liquid type rotation pack bed reaction system suitable for use in the present invention comprises: a driving motor 1, a transmission shaft 2, a pack bed 3 containing a network packing, and a rotation drum 4. Two liquid feeds are separately sprayed into the pack bed from the first inlet 5 and the second inlet 6. The first liquid feed introduced into the first inlet 5 enters the distribution dish 7, and is divided into tiny liquid drops which, together with the second liquid feed from the second inlet 6, enter the pack bed 3 by the driving of the centrifugal force, wherein the two liquid feeds are fully mixed and undergo a reaction. A gaseous by-product resulting from the reaction is discharged from the gas outlet 8, wherein said outlet 8 is installed with a branch pipe connected to an evacuation device (not shown in the drawing) to set up a vacuum environment for the reaction system. The liquid product is collected at the enclosure 16 of the main body, and is discharged from the liquid outlet 9.

When the liquid feeds enters the rotation pack bed 3 from the first inlet 5 and the second inlet 6, an inert gas (e.g. nitrogen, $CO_2$, argon or other gas that does not participate the reaction) is introduced into the rotation pack bed 3 from the gas inlet 10, which counter currently flows through the reaction mixture, and carries the gas by-product away from the reaction mixture to the gas outlet 8.

In order to prevent the inert gas from gas inlet 10 by-passing to the gas outlet 8, a sealing device 11, which adopts a maze-type seal, is installed, the gap of the seal teeth is adjustable. A mechanical shaft seal 12 is installed on said transmission shaft 2 to prevent a leakage caused by the pressure difference between the internal pressure of the system and the outside pressure. In order to reduce the amounts of the unreacted reactants in the product mixture flowing out of the system, an internal circulation pump 13, an internal circulation pipeline 14, and recycling ratio control valves 15 are installed.

The contents, objectives and features of the present invention are further elaborated by way of the following examples which are for explaining the present invention instead of limiting the scope thereof.

EXAMPLES 1–3
Batchwise Removal of HCl from TNPP (Tris Nonylphenol Phosphite)

The specifications of the pack bed used in these examples were: inside diameter 76 mm, outside diameter 160 mm, and thickness 33 mm. The rotation speed of the pack bed was fixed at 1300 rpm, and nitrogen was used as a carrying agent. The inlet position of TNPP was at a location 35 mm from the axis of the pack bed. 5 kg of TNPP (having an acid value of 0.18 mgKOH/g, and a viscosity of 1000 cps) was taken. The temperature of TNPP feed and the gas/liquid ratio of nitrogen to TNPP were altered as shown in Table 1. The results were also shown in Table 1. The test results indicated that the acid value of TNPP, after 15 minutes of processing (one cycle) by the rotation pack bed, was reduced to 0.06~0.08 mgKOH/g. After a consecutive treatment to 45 minutes (three cycles in total), the acid value of TNPP dropped to 0.04~0.06 mgKOH/g.

TABLE 1

| Example | | 1 | 2 | 3 |
|---|---|---|---|---|
| Acid value of feed | mg KOH/g | 0.18 | 0.18 | 0.18 |
| Acid value of discharge after 15 min. | mg KOH/g | 0.08 | 0.06 | 0.07 |
| Acid value of discharge after 45 min. | mg KOH/g | 0.06 | 0.05 | 0.04 |
| Temperature of feed | ° C. | 130 | 170 | 150 |
| Flow rate of inlet liquid | mL/min | 200 | 200 | 200 |
| Flow rate of inlet gas | L/min | 15 | 15 | 20 |
| Gas/liquid ratio | — | 75 | 75 | 100 |
| Rotation speed | rpm | 1300 | 1300 | 1300 |

EXAMPLE 4
Continuous Removal of HCl from TNPP

The specifications of the pack bed used in this example were: inside diameter 120 mm, outside diameter 600 mm, and thickness 100 mm. The rotation speed of the pack bed was fixed at 1200 rpm. The inlet of the TNPP feed was at a location 50 mm from the axis of the pack bed. The nitrogen temperature was 88° C., and the flow rate of nitrogen was 1250 l/min. The viscosity of TNPP was 1000 cps, the temperature of TNPP was 114° C., and the flow rate of TNPP was 25 l/min. Prior to the processing by the pack bed, the acid value of TNPP was 0.3 mgKOH/g; and the acid value decreased to 0.16 mgKOH/g after being processed.

What is claimed is:

1. A method for removing a volatile component from a high viscosity liquid by using a rotation pack bed, which comprises the following steps:

a) introducing a high viscosity liquid into a rotation pack bed rotating around an axis, said rotation pack bed being located in a housing and comprising a central channel region around said axis and an annular pack region surrounding said central channel region, said annular pack region being packed with a packing, and said annular pack region and said central channel region being in fluid communication only through a boundary thereof, and said annular pack region and said housing being in fluid communication only through an outer circumference of said annular pack region, wherein said high viscosity liquid is introduced to a location in said annular pack region so that said high viscosity liquid receives a sufficient centrifugal force at said location and can radially flow through said packing from said location in a direction away from said axis;

b) introducing a high pressure gas at a location near the outer circumference of said annular pack region, and/or connecting said central channel region to a suction source so that, when said highly viscous fluid radially flows through said packing, a volatile component in said high viscosity liquid together with aid high pressure gas or said volatile component per se flow out of said rotation pack bed and said housing in a gas phase from said central channel region; and c) collecting a purified liquid, which flows out from the outer circumference of said annular pack region, from a bottom of said housing, wherein said high viscosity liquid in step a) comprises tris nonylphenol phosphite, and hydrogen chloride contained in said tris nonylphenol phosphite, wherein said volatile component is said hydrogen chloride, and said purified liquid is a tris nonylphenol phosphite having a reduced amount of hydrogen chloride; or wherein said high viscosity liquid in step a) comprises polyurethane and an unreacted polyisocyanate monomer contained in said polyurethane, wherein said volatile component is said polyisocyanate monomer, and said purified liquid is a polyurethane having a reduced amount of polyisocyanate monomer.

2. The method according to claim 1, wherein said high viscosity liquid in step a) has a viscosity less than 3000 cps at room temperature.

3. The method according to claim 1, wherein said high viscosity liquid in step a) comprises tris nonyiphenol phosphite, and hydrogen chloride contained in said tris nonylphenol phosphite, wherein said volatile component is said hydrogen chloride, and said purified liquid is a tris nonyiphenol phosphite having a reduced amount of hydrogen chloride.

4. The method according to claim 1, wherein said high viscosity liquid in step a) comprises polyurethane and an unreacted polyisocyanate monomer contained in said polyurethane, wherein said volatile component is said polyisocyanate monomer, and said purified liquid is a polyurethane having a reduced amount of polyisocyanate monomer.

5. The method according to claim 1, wherein, in step b), a high pressure nitrogen gas is introduced into said housing as said high pressure gas.

6. The method according to claim 1 further comprising recycling a portion of the purified liquid in step c) to step a) and into said annular pack region.

7. The method according to claim 1, wherein, in step b), a high pressure gas is introduced into said housing, which contacts and reacts with the high viscosity liquid when said high viscosity liquid is radially flowing through said packing material, wherein a product of the chemical reaction, as said volatile component, together with unreacted high pressure gas flows out said rotation pack bed and said housing in a gas phase from said central channel region, and another product of the chemical reaction is collected at the bottom of said housing together with unreacted high viscosity liquid.

8. A method for removing a volatile component from a high viscosity liquid by using a rotation pack bed, which comprises the following steps:
   a) introducing a high viscosity liquid into a rotation pack bed rotating around an axis, said rotation pack bed being located in a housing and comprising a central channel region around said axis and an annular pack region surrounding said central channel region, said annular pack region being packed with a packing, and said annular pack region and said central channel region being in fluid communication only through a boundary thereof, and said annular pack region and said housing being in fluid communication only through an outer circumference of said annular pack region, wherein said high viscosity liquid is introduced to a location in said annular pack region so that said high viscosity liquid receives a sufficient centrifugal force at said location and can radially flow through said packing from said location in a direction away from said axis;
   b) introducing a high pressure inert gas at a location near the outer circumference of said annular pack region, and/or connecting said central channel region to a suction source so that, when said highly viscous fluid radially flows through said packing, a volatile component in said high viscosity liquid together with said high pressure inert gas or said volatile component per se flow out of said rotation pack bed and said housing in a gas phase from said central channel region; and
   c) collecting a purified liquid, which flows out form the outer circumference of said annular pack region, from a bottom of said housing;

wherein step a) further comprises introducing a liquid reactant from said central channel region to said rotation pack bed, said liquid reactant flowing through said packing in a radial direction away from said axis by a centrifugal force, and said liquid reactant and said high viscosity liquid generating a chemical reaction, wherein a product of the chemical reaction, as said volatile component, flows out of said rotation pack bed and said housing in a gas phase, and another product of the chemical reaction, unreacted high viscosity liquid and unreacted liquid reactant are collected at the bottom of said housing, wherein said high viscosity liquid comprises nonylphenol, said liquid reactant comprises $PCl_3$, said high pressure inert gas is nitrogen, said product of the chemical reaction is HCl which flows out of said rotation pack bed from said central channel region in a gas phase together with the nitrogen, and said another product of the chemical reaction is tris nonylphenol phosphite which, together with unreacted nonylphenol and $PCl_3$, is collected at the bottom of said housing.

* * * * *